US00PP18180P3

(12) United States Plant Patent
Olesen

(10) Patent No.: US PP18,180 P3
(45) Date of Patent: Nov. 6, 2007

(54) FLORIBUNDA ROSE PLANT NAMED 'POULCAS026'

(50) Latin Name: *Rosa hybrida*
Varietal Denomination: Poulcas026

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 3 days.

(21) Appl. No.: 11/395,550

(22) Filed: Mar. 31, 2006

(65) Prior Publication Data

US 2007/0234445 P1 Oct. 4, 2007

(51) Int. Cl.
*A01H 5/00* (2006.01)

(52) U.S. Cl. ..... Plt./150

(58) Field of Classification Search ..... Plt./150
See application file for complete search history.

*Primary Examiner*—Kent Bell
*Assistant Examiner*—S. B. McCormick-Ewoldt

(57) ABSTRACT

A new garden rose plant of the floribunda class which has abundant, red flowers and attractive foliage. This new and distinct variety has shown to be uniform and stable in the resulting generations from asexual propagation.

1 Drawing Sheet

Botanical designation: *Rosa hybrida.*
Variety denomination: 'Poulcas026'.

SUMMARY OF THE INVENTION

The present invention constitutes a new and distinct variety of garden rose plant which originated from a controlled crossing between the female seed parent, 'Poulgrad', U.S. Plant Pat. No. 11,610, and the male pollen parent, an unnamed seedling.

The two parents were crossed during the summer of 1997 and the resulting seeds were planted in a controlled environment in Fredensborg, Denmark. The new variety, named 'Poulcas026', originated as a single seedling from the stated cross.

The new variety may be distinguished from its female seed parent by the following combination of characteristics:

1. The seed parent has 25 to 30 petals with no petaloids. 'Poulcas026' has 26 petals total, 5 to 8 of which are petaloids.
2. Flowers of the seed parent have a general tonality of Red Group 53A–46A, wile flowers of 'Poulcas026' are Red Group 46A to 46B.

The new variety may be distinguished from its male pollen parent by the following combination of characteristics:

1. The pollen parent has more flower petals than 'Poulcas026'.
2. Plants of the pollen parent are less compact than 'Poulcas026'.

The objective of the hybridization of this rose variety was to create a new and distinct variety for garden use with unique qualities, such as:

1. Uniform and abundant red flowers which maintain good color for the life of the flower;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas026' from all other varieties of which we are aware.

As part of the rose development program, Mogens N. Olesen germinated the seeds from the aforementioned hybridization during winter of 1997 and conducted evaluations on the resulting seedlings in a controlled environment in Fredensborg, Denmark. 'Poulcas026' was selected in the spring of 1998 by the inventor as a single plant from the progeny of the aforementioned hybridization.

Asexual reproduction of 'Poulcas026' by traditional budding and rooted cuttings was first done by Mogens N. Olesen in the nursery in Fredensborg, Denmark in July, 1998. This initial and other subsequent asexual propagations conducted in controlled environments have demonstrated that the characteristics of 'Poulcas026' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcas026'. Specifically illustrated in the drawing are.

DETAILED DESCRIPTION OF THE VARIETY

Figures 1A, 1B, 1C, 1D, 1E, 1F:
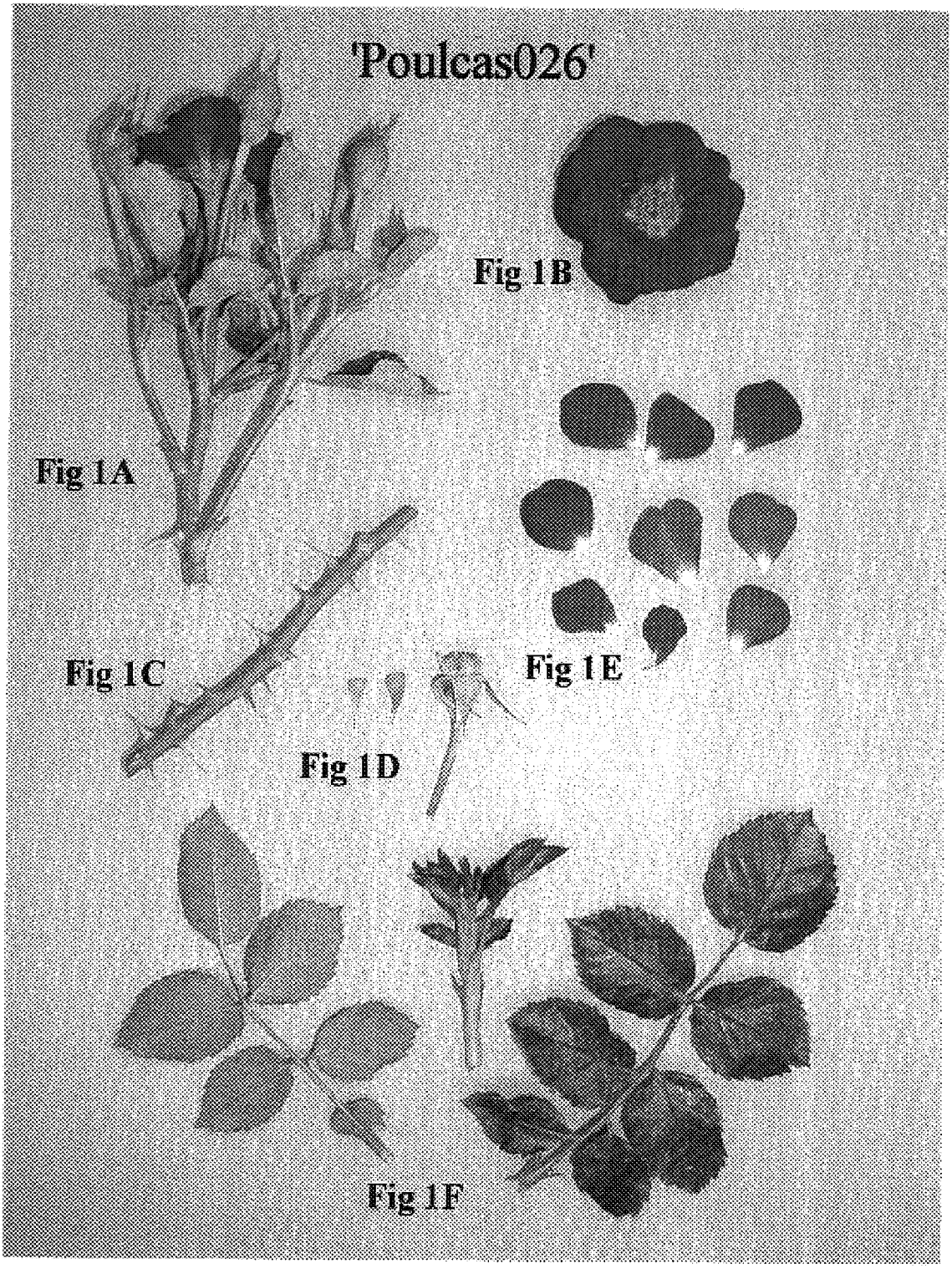
FIG. 1A; Cluster of flower buds showing pedicels, peduncles, receptacles, as well as single open blossom viewed from the side.
FIG. 1B; Open flower viewed from above, as well as flower petals, detached.
FIG. 1C; Bare stem exhibiting prickles.
FIG. 1D; Sepals, receptacle, and peduncle.
FIG. 1E; Juvenile leaves.
FIG. 1F; Mature leaves.

The following is a description of 'Poulcas026', as observed in its growth in in a field nursery in Jackson County, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulzin', U.S. Plant Pat. No. 11,626 are compared to 'Poulcas026' in Chart 1.

CHART I

| | 'Poulcas026' | 'Poulzin' |
|---|---|---|
| Petal Count | 26 petals total, 5 to 8 of which are petaloids | Over 60 petals under normal conditions with 5-10 petaloids |
| Flower Diameter | 50 to 55 mm | 50 to 60 mm |
| Color of outer petals upper surface, upon opening | Red Group 46A to 46B with occasional streaks of White Group 155A and Red Group 43B | 45B with intonations of Red-Purple Group 57C |

FLOWER AND FLOWER BUD

Blooming habit: Continuous.

Flower bud:

*Size.*—Upon opening, 23 mm in length from base of receptacle to end of bud. Bud diameter is 10 mm.

*Bud form.*—Pointed ovate.

*Bud color.*—As sepals unfold, petals are Red Group 53A.

*Sepal inner surface.*—Color: Yellow-Green Group 146C. Surface: Medium pubescence observed.

*Sepal outer surface.*—Color: Yellow-Green Group 144A. Anthocyanic pigments of Greyed-Red Group 180B. Texture: Somewhat pubescent.

*Sepal shape.*—Apex: Cirrhose. Base: Flat at union with receptacle.

*Sepal Margin.*—Margins have weak foliaceous appendages on three of the five sepals.

*Sepal size.*—20 mm long by 7 mm wide.

*Receptacle.*—Texture: Smooth. Shape: Urn-shaped. Size: 7 mm (h)×7 mm (w). Color: Yellow-Green Group 144A.

*Peduncle.*—Surface: Smooth. Length: 40 to 45 mm. Diameter: Normally 3 mm. Color: Yellow-Green Group 144A and 145B. Anthocyanic pigments of Greyed-Red Group 178A. Strength: Somewhat strong.

Flower bud development: Flower buds are borne singularly or in clusters of an average of 7 flower buds per stem. Inflorescence type is a corymb.

Flower bloom:

*Fragrance.*—None.

*Duration.*—The blooms have a duration on the plant of approximately 10 to 12 days. Petals fall cleanly away from plant after flowers have fully matured.

*Size.*—Flower diameter is 50 to 55 mm when open. Flower depth is 17 to 22 mm.

*Flower shape.*—Generally, flowers are shaped like a open cup with loosely arranged petals curving outward from the center.

*Shape of flower, side view.*—Upon opening the upper portion is a flattened convex. The lower portion is concave. After opening, the upper portion is a flattened convex. The lower portion is concave.

*Petalage.*—Under normal conditions, flowers have 26 petals total, 5 to 8 of which are petaloids.

*Petal color.*—Upon opening, outer petals Upper surface: Red Group 46A to 46with occasional streaks of White Group 155A and Red Group 43B. Lower surface: Red-Purple Group 58B with intonations of Red Group 61B with occasional streaks of Red-Purple Group 58C. Upon opening, inner petals: Upper surface: Red Group 46A to 46B with occasional streaks of White Group 155A and Red Group 43B. Lower surface: Red-Purple Group 58B with intonations of Red Group 61B with occasional streaks of Red-Purple Group 58C. Basal petal spots, upon opening: Upper surface: Yellow Group 4A. Lower surface: Yellow Group 4A. After opening, outer petals Upon opening, outer petals Upper surface: Red Group 46A to 46B with occasional streaks of White Group 155A and Red Group 43B. Lower surface: Red Group 58B with intonations of Red Group 61B with occasional streaks of Red-Purple Group 58C. Upon opening, inner petals: Upper surface: Red Group 46A to 46B with occasional streaks of White Group 155A and Red Group 43B. Lower surface: Red Group 58B with intonations of Red Group 61B with occasional steaks of Red-Purple Group 58C. Basal petal spots, after opening: Upper surface: Yellow Group 4D to White Group 155A. Lower surface: Yellow Group 4D to White Group 155A.

General tonality: On open flower Red Group 46A to 46B. No change in the general tonality at the end of the 10th day.

Petals:

*Petal reflex.*—Reflexed.

*Margin.*—Entire and uniform. Occasionally there is a point or cleft at the center of the margin.

*Shape.*—Generally narrow elliptical to broad elliptical. Apex shape: Orbicular. Base shape: Acute.

*Size.*—Normally 25 mm (l)×20 mm (w).

*Texture.*—Smooth.

*Thickness.*—Average.

*Arrangement.*—Not Formal.

Petaloids:

*Quantity.*—5 to 8.

*Shape.*—Narrow elliptical to irregular and asymmetrical.

*Color.*—Upper surface: Red Group 53A with basal petal spots of Yellow Group 4A. Lower surface: Red Group 58B with intonations of Red Group 61B with basal petal spots of Yellow Group 4A.

*Size.*—Normally 8 to 12 mm (l)×10 mm (w).

Reproductive Organs:

*Pollen.*—None observed.

*Anthers.*—Size: 2 mm in length. Color: Yellow-Orange Group 21A. Quantity: 120 average.

*Filaments.*—Color: Yellow Group 12A. Length: 5 mm.

*Pistils.*—Length: 5 to 6 mm. Quantity: 110.

*Stigmas.*—Superior in location relative to the length of the filaments and the height of the anthers. Color: Greyed-Yellow Group 162D.

*Styles.*—Color: Green-White Group 157A and Red-Purple Group 58B toward the stigma.

*Hips.*—None Observed in the field nursery in Jackson County Oregon.

Plant

Plant growth: Upright to bushy. When grown as a budded field grown plant on *Rosa multiflora* understock, the height of the plant is 60 to 100 cm and the average width is 75 cm.

Stems:

*Color.*—Juvenile growth: Yellow-Green Group 144B. Mature growth: Yellow-Green Group 146A.

*Length.*—On average, canes are 60 cm from the base of the plant to the flowering portion.

*Diameter.*—Normally 6 mm.

*Internodes.*—On mature canes, there is an average distance of 30 mm between nodes.

*Surface texture.*—Young wood: Smooth. Older wood: Smooth.

Prickles:

*Incidence.*—13 prickles per 10 cm of stem.

*Size.*—Average length of prickles on mature stems is 8 mm.

*Shape.*—Upper side: Flat. Lower side: Slightly concave.

*Color.*—Juvenile prickles: Yellow-Group 151A with intonations of Yellow-Green Group 144B.

Plant foliage: Normal number of leaflets leaves in middle of the stem: 7 leaflets.

*Compound leaf.*—130 mm (l)×80 mm (w).

*Quantity.*—3 leaves per 10 cm of stem on average.

*Color of mature foliage.*—Upper side: Yellow-Green Group 147A. Lower side: Yellow-Green Group 147B.

*Color of juvenile foliage.*—Upper side: Yellow-Green Group 146B with strong anthocyanic intonations of Greyed-Purple Group 183A. Lower side: Yellow-Green Group 146B with strong anthocyanic intonations of Greyed-Purple Group 183A.

Plant leaves and leaflets:

*Stipules.*—Size: 17 mm in length. Shape: Linear, slightly broad based with outward extending apecies. Margins: Finely serrated with few stipitate glands. Color: Yellow-Green Group 146A. Anthocyanin: None observed.

*Petiole.*—Length: Normally 27 mm. Diameter: Normally 2 mm. Upper surface: Color: Greyed-Yellow Group 160B. Lower surface: Color: Yellow-Green Group 146B. Observations: Prickles 2 to 3 mm in length.

*Rachis.*—Length: 65 mm. Upper surface: Color: Yellow-Green Group 146A. Lower surface: Color: Yellow-Green Group 146B. Observations: Prickles 2 to 3 mm in length observed.

*Leaflet.*—Edge: Serrated. Size: Average size of the terminal leaflet on normal leaves is 40 mm in length by 35 mm wide. Shape: Generally ovate to orbicular. Base: Rounded. Apex: Acuminate.

*Texture.*—Smooth.

*Thickness.*—Average.

*Arrangement.*—Odd pinnate.

*Venation.*—Reticulate.

*Glossiness.*—Somewhat glossy.

Disease resistance: Above average resistance to powdery and downy mildew, rust, black spot, and *Botrytis* under normal growing conditions in Jackson County, Oreg.

Cold hardiness: The variety is tolerant to USDA Cold Hardiness Zone 6.

Heat tolerance: The variety has been found to be suitable for climate conditions found in the American Horticulture society heat zone 7.

It is claimed:

1. A new and distinct variety of rose plant of the floribunda rose class named 'Poulcas026', substantially as illustrated and described herein, due to its abundant red flowers, disease resistance, and extended period of bloom.

* * * * *

'Poulcas026'